United States Patent

Sabin et al.

[11] Patent Number: 5,984,953
[45] Date of Patent: Nov. 16, 1999

[54] SELF-REGULATING HEAT PACK

[75] Inventors: Martin W. Sabin, Nokomis; Cullen M. Sabin, Bradenton, both of Fla.

[73] Assignee: Tempra Technology, Inc., Bradenton, Fla.

[21] Appl. No.: 09/083,005

[22] Filed: May 21, 1998

[51] Int. Cl.[6] ...................................................... A61F 7/00
[52] U.S. Cl. ................... 607/114; 607/108; 62/4
[58] Field of Search .................. 607/108, 109, 607/110, 111, 114; 62/530, 4

[56] References Cited

U.S. PATENT DOCUMENTS

| | | |
|---|---|---|
| 3,804,077 | 4/1974 | Williams . |
| 3,977,202 | 8/1976 | Forusz et al. ................................. 62/4 |
| 4,049,408 | 9/1977 | Patel ............................................. 62/4 |
| 4,081,256 | 3/1978 | Donnelly ...................................... 62/4 |
| 4,397,315 | 8/1983 | Patel . |
| 4,462,224 | 7/1984 | Dunshee et al. ........................... 62/530 |
| 4,780,117 | 10/1988 | Lahey et al. ................................. 62/4 |
| 4,967,573 | 11/1990 | Wilhelm ................................... 62/530 |
| 5,035,230 | 7/1991 | Steidl et al. . |
| 5,391,198 | 2/1995 | Cheney, III et al. ................... 607/114 |
| 5,423,996 | 6/1995 | Salyer ......................................... 252/70 |
| 5,478,988 | 12/1995 | Hughes et al. ........................... 219/730 |
| 5,534,020 | 7/1996 | Cheney, III et al. .................... 607/118 |
| 5,545,197 | 8/1996 | Bowen ...................................... 607/108 |
| 5,552,075 | 9/1996 | Salyer ......................................... 252/70 |
| 5,611,329 | 3/1997 | Lamensdorf ......................... 126/263.07 |
| 5,650,090 | 7/1997 | Salyer ......................................... 252/70 |

OTHER PUBLICATIONS

Livage, J., et al., Sol–Gel Chemistry of Transition Metal Oxides, *Prog. Solid St. Chem.*, 18:259 (1988).
U.S. Patent Application 09/021,927, by Sabin et al., filed Feb. 11, 1998.

*Primary Examiner*—Lee Cohen
*Assistant Examiner*—Rosiland Kearney
*Attorney, Agent, or Firm*—Fish & Richardson P.C.

[57] ABSTRACT

The invention relates to a self-heating, disposable heating pack utilizing an exothermic chemical reaction. Self-moderation of the heat pack is provided through the use of a preformed reversibly stiffenable gel that alters the rate of exothermic chemical reactions. A vaporizable solvent is used to adjust the gel stiffness. The heat pack can be used in heat transfer or ambient temperature conditions which differ from those anticipated as design conditions.

35 Claims, 2 Drawing Sheets

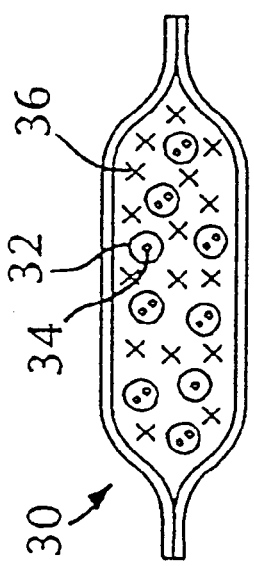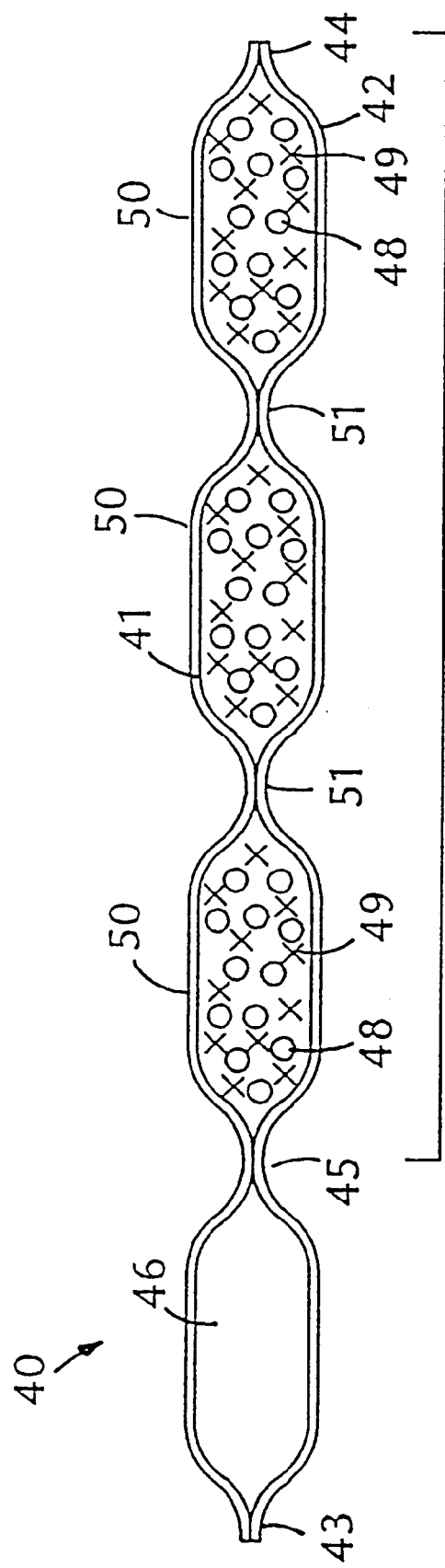
FIG. 3
FIG. 4

SELF-REGULATING HEAT PACK

BACKGROUND OF THE INVENTION

The invention relates to self-heating devices for providing heating by exothermic chemical reactions.

Compact, self-heating devices that produce heat through exothermic chemical reactions are known to the art. U.S. Pat. No. 4,397,315 discloses a device having an outer envelope and an inner envelope, with the outer envelope containing sodium thiosulfate, and the inner envelope containing ethylene glycol. The walls of the inner envelope are rupturable, allowing the contents of each envelope to mix. U.S. Pat. No. 5,035,230 discloses a heat pack having two compartments separated by a frangible seal. Potassium permanganate oxidizing agent coated with sodium silicate is provided in one zone of the heat pack, and aqueous ethylene glycol fuel is provided in the other zone. In operation of the device, the seal is compromised to allow the reactants to come in contact with each other.

Devices for producing heat or cold by heat of Hdilution rather than by chemical reaction are also known. U.S. Pat. No. 3,804,077 describes a heat pack which contains calcium chloride, a water soluble chemical and starch, a gelling agent, in one zone, and water in another zone.

A characteristic feature of a heat pack is the attainment of an operating temperature as measured on the surface of the heat pack. The operating temperature depends on the balance between the heating rate (heat generation rate) and the cooling rate (heat transfer to the surroundings). In the best heat packs according to the prior art, the presence or absence of a heat absorbing body external to the heat pack and the rate of heat loss did not affect the progress of the exothermic chemical reaction. Thus, a heat pack according to the prior art achieved a stable balance between heat generation within the pack and heat transfer to the pack's surroundings only for an intended, or design, rate of heat loss. The design rate of heat loss does not occur in every instance. In particular, if heat transfer to the surroundings is less than intended by design (a poorly cooled pack), the rate of heat generation in the pack and the consequent temperature rise are relatively excessive in that instance. Situations in which heat loss below design can occur are high ambient temperature or low thermal mass in the heat sink (low ΔT). Another situation is poor physical contact to a heat sink (low heat transfer coefficient). When poorly cooled, packs of the prior art are prone to produce temperatures higher than intended and excessive buildup of pressure (e.g., vapor pressure, such as from steam) can cause the pack to rupture, sometimes explosively.

SUMMARY OF THE INVENTION

This invention includes devices and methods for heating. Devices according to this invention include a disposable heat pack that provides heat through a self-moderating exothermic chemical reaction between particular reactants. The heat pack includes a disposable container divided into two types of liquid and gas impermeable zones. The zone of the first type contains a substantially solid and particulate oxidizing agent embedded in, and dispersed throughout, solid pieces of a dissolvable binding agent, and can also contain a substantially solid and particulate soluble secondary fuel. The zone of the second type contains a liquid mixture comprising a primary fuel, a preferably preformed stiffenable gel and a solvent. Between the two types of zones is a separator. The separator is operated or compromised to establish communication between the two types of zones. The container is designed to include vapor space and a condensation surface over the reaction medium during operation of the heat pack.

Upon operation or compromise of the separator, communication is established between the zones, thereby bringing the contents of the two zones, and hence the oxidizing agent and the primary fuel, into contact with each other. This initiates a first exothermic chemical reaction, the rate of which is moderated by known means to achieve a desired rate of reaction and amount of temperature rise. Moderation for normal operation at an intended ambient temperature and an intended heat loss is achieved by the controlled exposure of the chemical reactants at a predetermined rate through the dissolving of a binding agent which surrounds one or both of the chemical reactants. Contact between the two zones also initiates dissolution of the secondary fuel by the solvent. The secondary fuel dissolves up to its saturation concentration and migrates toward the oxidizer. The first exothermic reaction provides sufficient energy to initiate a second exothermic reaction between dissolved secondary fuel and oxidizer exposed by dissolution of the binding agent. The second exothermic reaction is moderated for normal operation similarly to the first exothermic reaction.

However, the second exothermic reaction is further moderated in the event of a high temperature excursion due to heat loss from the pack being lower than the anticipated, or design, rate of heat loss. High temperature causes evaporation of solvent, which condenses on exposed inner surfaces of the pack above the reaction mixture. This causes the preformed gel to stiffen, slowing migration of fuels to the oxidizer and reducing the rate of heat generation of the exothermic reactions. Thus, the heat pack according to this invention is self-moderating in response to conditions such as abnormally high ambient temperature or other external conditions that lower the rate of heat loss from the pack below the design rate. The moderating mechanism is reversible. If the temperature falls, evaporated solvent returns to the gel, reducing its stiffness and increasing the rate of reaction between the primary and secondary fuels and the oxidizer.

In one aspect, the present invention features a disposable heating device, including a disposable container having at least one liquid- and gas-impermeable first zone and at least one liquid- and gas-impermeable second zone. The container can include a thin-walled envelope that conforms to the shape of its surroundings, and can be made of a polymeric material, for example. The container also has a separator between the two zones, and the separator can be operated to allow communication between the zones. The separator can be a single use frangible membrane, for example.

The second zone includes as its contents a primary fuel (for example, a polyhydroxy compound such as glycerine), a preformed stiffenable gel (for example, an organic gel such as starch), and a vaporizable solvent (for example, water). The gel is of a type that stiffens when solvent is removed from it (for example, by vaporization of the solvent), and is present in an amount sufficient to prevent the temperature of the device from overshooting a predetermined maximum temperature.

The first zone includes as its contents a substantially solid and particulate oxidizing agent (for example, an alkali metal salt of a permanganate, such as potassium permanganate), and optionally, a secondary fuel (for example, a polyhydroxy compound, such as a sugar). The oxidizing agent is embedded in and dispersed throughout a binding agent that is dissolvable in at least one of the vaporizable solvent and the primary fuel.

To operate the device, the separator is operated to allow the contents of the zones to communicate and mix. The binding agent dissolves during operation of the device to controllably expose the oxidizing agent to the fuel at a predetermined rate. An exothermic chemical reaction (for example, an oxidation-reduction reaction) is initiated at ambient temperature, and heat is produced. This reaction can proceed in various environments (for example, in an aqueous environment).

The container includes a vapor space into which the vaporizable solvent vaporizes and a condensation surface above the contents of the zones onto which the vaporized solvent condenses. This is designed to occur as the temperature of the device approaches a predetermined maximum temperature, and the removal of solvent from the preformed stiffenable gel causes it to stiffen.

The device can also contain a temperature stabilizing means in either of the zones (for example, a phase change material such as a paraffinic hydrocarbon).

In another aspect, the invention features a method of heating objects with the device. This method involves contacting the device of the invention with an object to be heated, operating the separator to activate the device as described above, and allowing the contents to mix. In another aspect of the invention, the separator can be operated before the device and object come into contact with each other. The objects to be heated can be food or drink, containers containing food or drink, humans or animals, including human or animal medical patients (for example, surgical patients), or articles of clothing or footwear.

The heat pack of the present invention has several advantages compared to those of the prior art.

The heat packs of the present invention, while providing an exothermic chemical reaction useful for heating objects, simultaneously also provide moderation of exothermic chemical reactions between an oxidizing agent and primary and secondary fuels during normal operation and protection against temperature excursions. This advantage allows far better control of the performance characteristics of heat packs than previously possible, in particular, control of the maximum temperature and rate of heat generation.

The heat packs of the present invention are able to achieve and, by self regulation, maintain a peak temperature, determined by the contents of the heat packs, despite unusually low heat loss. By this self regulation, heat packs according to the invention are able to achieve a desired peak temperature over a greater range of ambient conditions than previously known heat packs. This advantage of accommodating varying ambient temperatures is critical to a number of applications, including those involving the heating of living systems, which tend to undergo cell damage at temperatures above about 42.2° C. Also, the standardized preparation of meals, for example, in remote locations is facilitated by such a property, possessed by the heat packs of the invention. Heaters designed to provide heat for meals-ready-to-eat (MREs) used in the armed forces are known in the art. U.S. Pat. No. 5,611,329 discloses a flameless ration heater utilizing an exothermic chemical reaction between water and a magnesium-iron alloy.

The heat packs of the present invention employ increased viscosity in the form of a flowable liquid, preferably a gel, which is self-adjusting in its viscosity or stiffness to control the heat generation of the exothermic chemical reaction. A gel as used in the heat packs is preformed, that is, the gel is formed before the device is activated. This allows the opportunity to moderate the exothermic chemical reaction immediately.

The heat-producing contents of preferred embodiments of the heat pack of the invention do not fall to the bottom of the heat pack under the influence of gravity. This means that the distribution of heat within the heat pack of the invention is uniform, and the heat pack does not need to be continually kneaded to eliminate uneven heat distribution.

Upon completion of the exothermic reaction or reactions which takes place inside of the heat pack of the present invention, the pack preferably does not contain any soluble toxic or environmentally undesirable reactants or reaction products. Thus, the container can be safely discarded in a landfill with no danger to the environment. This is in sharp contrast to certain other self-heating devices, which contain soluble toxic or environmentally undesirable byproducts.

Other features and advantages of the invention will be apparent from the following detailed description, and from the claims.

BRIEF DESCRIPTION OF THE DRAWING

FIG. 3 is a cross sectional view of a zone of the first type in a particular embodiment of a heat pack of the invention.

FIG. 4 is a cross sectional view of a particular embodiment of a heat pack of the invention.

DETAILED DESCRIPTION OF THE INVENTION

Figure 1:
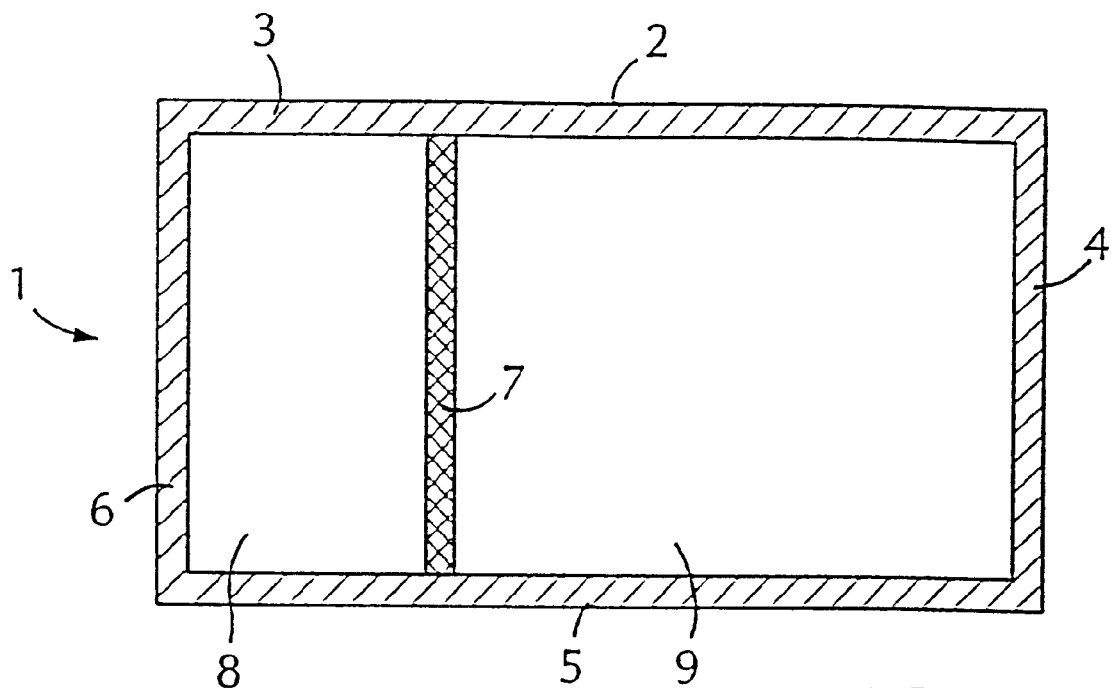
FIG. 1 is an overhead view of a particular embodiment of a heat pack of the invention, having a single zone for each reactant.

The disposable heat pack of the present invention is of the type that operates on the principle of evolution of the heat of reaction between complementary pairs of chemical entities. In preferred embodiments, the exothermic chemical reaction is an oxidation/reduction reaction resulting upon contact of oxidizing and reducing agents with each other. Compatible pairs of chemical entities are required, one member of the pair acting as an oxidizing agent, and the other member of the pair acting as a reducing agent, often referred to as a fuel. Multiple oxidizing agents and/or fuels are also envisioned in the heat packs of the present invention.

The use of a chemical reaction for heat generation presents significant difficulties. An oxidizing agent itself may be highly reactive and cause combustion, if not protected sufficiently. The exothermic reaction of a pack capable of generating an amount of heat needed for typical applications, if not moderated, leads to the very rapid production of heat, causing excessive, uncontrolled temperature rise, a serious drawback which can be difficult to avoid. Rapid production of heat is not the most desirable heat profile for many applications and, moreover, can be hazardous. In light of these difficulties, it is important to moderate the production of heat in the heat pack.

Heat packs utilizing oxidation/reduction reactions are disclosed in U.S. Pat. No. 5,0350,230 (the "'230 patent"), which is incorporated by reference herein in its entirety. The device of the '230 patent has two separated zones. One zone contains a dry reactant, i.e., short cylinders comprising potassium permanganate crystals within a sodium silicate binding agent. The other zone contains an ethylene glycol/ water solution, which serves as a fuel mixture. In certain embodiments, the fuel serves as a solvent, eliminating the need for a separate solvent. The two zones are separated, for example, by a frangible seal that is meant for single-use. When the seal between the two zones is ruptured, the fuel solution flows to the oxidizing agent pellets and reaction occurs. The rate of reaction, and hence the rate of heat production, is moderated by the rate of dissolution of the binding agent, as dissolution is required to expose the oxidizer to the fuel.

For a given rate of heat loss to be encountered normally in an intended application, a heat pack according to the '230 patent can be designed to generate heat at a given rate and reach a given peak operating temperature. So long as the rate of heat loss is as anticipated, rate of temperature rise, peak temperature and duration of heating are predictable. However, if the rate of heat loss is not as intended, temperature rise will also vary, generally undesirably. Unpredictability arises if the ambient temperature and/or heat transfer from the heat pack are much different from that which was anticipated.

In heat packs according to the instant invention, a dissolvable binding agent as taught by '230 patent is utilized. Additionally, a preformed stiffenable gel is present to affect the rate of reaction. By adjustment of these two rate-controlling features, persons skilled in the art will be able to select and achieve rates of temperature rise and operating temperature in packs according to the present invention.

The modulation of the exothermic chemical reactions takes place through certain reversible physical changes of the reaction medium in order to produce the self-regulating effects desired in the heat packs of the invention. Modulation must occur to prevent the exothermic chemical reaction from raising the operating temperature of the heat pack above a predetermined maximum temperature ($T_{max}$). Modulation also acts to increase the rate of an ongoing exothermic reaction when the container temperature falls low enough to reverse the physical changes of the reaction medium. The $T_{max}$ will lie above the design peak operating temperature of the heat pack, which depends on the intended use of the pack. $T_{max}$ for the heat packs of this invention will depend on and be limited by what temperature above the design peak temperature can be tolerated for a particular use, and will generally be from about 1° C. to about 20° C. above the desired peak operating temperature of the pack. Considerations may be given to comfort or safety to the user, integrity of the container, or other factors apparent to persons skilled in the art when selecting $T_{max}$.

The heat packs of the present invention include a disposable container which is divided into two types of zones. Heat packs according to this invention comprise physically separated zones, or compartments, containing components that include chemical reactants. There is at least one zone of each type. The zone of the first type comprises an oxidizing agent and, in certain preferred embodiments, a fuel, referred to as a secondary fuel. The zone of the second type comprises a fuel, referred to as a primary fuel, a preformed stiffenable gel, and a vaporizable solvent. The zones are separated by a compromisable separator such as a valve or frangible seal. Upon compromise of the separator, communication between the zones is established and the contents of the zones contact each other. This contact allows the oxidizing agent, fuels and solvent to create a reaction medium. The oxidizing agent is preferably bound in, and dispersed throughout, a dissolvable binding agent, which selectively exposes the oxidizing agent to the reaction medium containing the fuels. This provides a moderated exothermic chemical reaction.

Referring to FIG. 1, there is displayed a cross sectional view of one embodiment of a heat pack of the present invention. The heat pack 1 is composed of a container having an upper sheet 2 and a lower sheet (not shown). The sheets are sealed together at the edges by edge seals 3, 4, 5, and 6. These edge seals are preferably made so that they are not readily opened by the consumer. A compromisable separator 7 is disposed from one edge seal of the heat pack 3 to another edge seal 5, thus dividing the heat pack 1 into two zones, 8 and 9. The separator is made to be compromised by the user. The heat container is designed to include a space for vapor above the reactants when the heat pack is in use.

Figure 2:
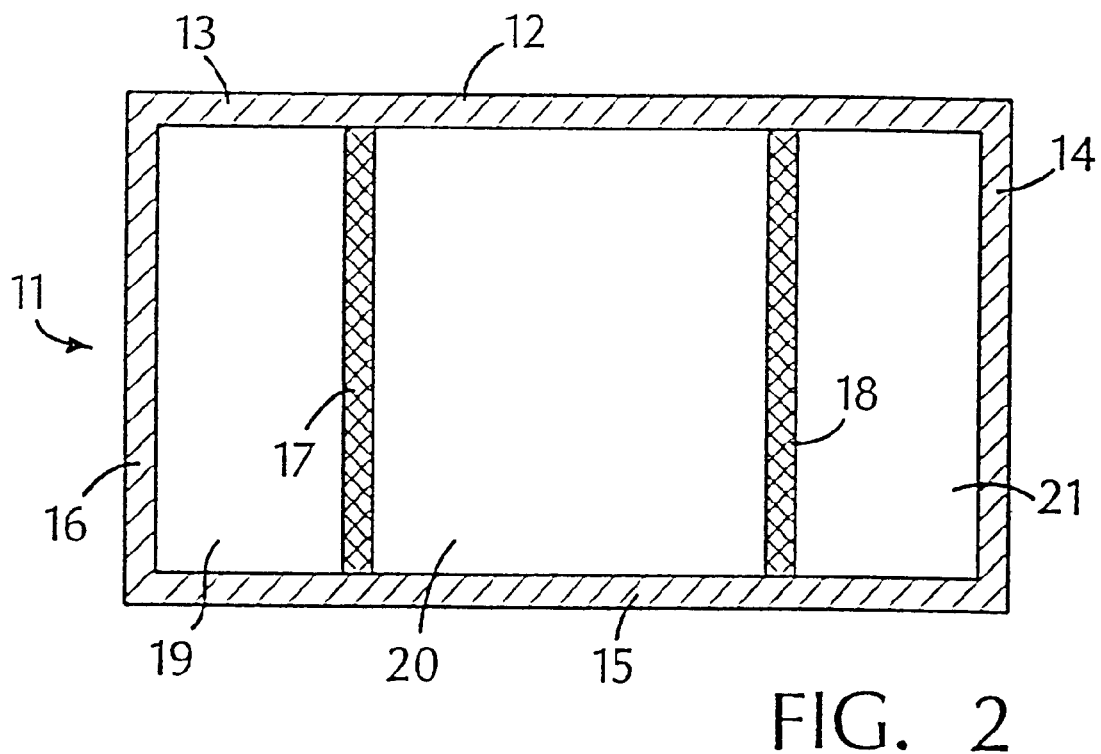
FIG. 2 is an overhead view of another particular embodiment of a heat pack of the invention, having multiple reactant zones.

Alternate embodiments of the device are also contemplated. For example, there may be more than one frangible seal, resulting in a device divided into more than two zones. An example of this is depicted in FIG. 2, which is another embodiment of a heat pack of the present invention. The heat pack 11 is composed of a container having an upper sheet 12 and a lower sheet (not shown). The sheets are sealed together at the edges by edge seals 13, 14, 15, and 16. These edge seals are preferably made so that they are not readily opened by the consumer. A pair of compromisable separators 17 and 18 is disposed from one edge seal of the heat pack 13 to another edge seal 15, thus dividing the heat pack 11 into three zones, 19, 20 and 21. The separators are made to be readily compromised by the user.

FIG. 3 shows the contents of a zone of the first type according one embodiment of a heat pack of the invention. Zone 30 contains an oxidizing agent, a dissolvable binding agent or binding agent, and a secondary fuel. Particles of solid binding agent 32 contain dispersed particles of substantially solid oxidizing agent 34. Also within the zone 30 are particles of the solid, soluble secondary fuel 36.

FIG. 4 shows another embodiment of a heat pack of the present invention. The heat pack comprises a generally rectangular container 40 having a top sheet 41 and a bottom sheet 42. Sheets 41 and 42 are sealed together with a peripheral edge seal, portions of which are shown at 43 and 44 (other portions not shown). The edge seal is preferably made so that it is not readily opened by the consumer. A compromisable separator 45 extends across container 40 from one side of the edge seal to the opposing side of the edge seal, thus dividing heat pack container 40 into two zones, 46 and 47. Separator 45 is made to be readily compromised by the user. Zone 47 contains oxidizing agent 48 and secondary fuel 49, and is vacuum sealed upon its construction. During manufacture of the heat pack, the mixture of oxidizing agent 48 (which may be dispersed in a binding agent, see FIG. 3) and secondary fuel 49 is distributed as a series of strips 50 extending across container 40. Vacuum packaging produces regions 51 of zone 47 where no mixture of oxidizing agent or secondary fuel is located. These regions allow the top sheet 41 and bottom sheet 42 to contact each other. During operation of the device, that is, after opening or compromise of the separator 45, slight gaseous pressure inside the container from the exothermic chemical reaction causes the sheets to separate from each other, effectively increasing the volume of the zone 47. This creates a vapor space and a surface above the reaction medium which is required in the heat packs of the invention.

The first, or primary, stage of reaction between the oxidizing agent and primary fuel is initiated readily upon contact of the oxidizing agent and the primary fuel within a range of ambient temperatures that may be encountered, for example, a range from −10 to 50° C. These ambient temperatures are sufficient to allow the primary exothermic chemical reaction to proceed either at once, or reasonably promptly, if there are rate-affecting barriers associated with one or both of the reaction partners. An example of such a barrier is a dissolvable binding agent surrounding one or both reaction partners. The primary reaction is preferably moderated by a dissolvable binding agent or a gel.

Many oxidizing agents are capable of generating suitable energies upon reaction with a corresponding fuel for use in the packs and methods of this invention. Preferred oxidizing agents are those comprising the alkali metal salts of the oxides of manganese and chromium, such as potassium permanganate, and potassium chromate. Other suitable oxidizing agents are pyridinium dichromate, ruthenium tetroxide and chromic acid, as well as a host of other oxidizing agents known to those skilled in the art. The choice of oxidizing agent is preferably made with disposability as a high priority. After use of the heat pack, we prefer that the residue not contain any soluble toxic or environmentally undesirable components. Our most preferred oxidizing agent is potassium permanganate.

The available surface area of the oxidizing agent is an important factor in the reactivity of the oxidizing agent in a reaction medium. Surface areas of solids are highly dependent on the physical form of the solid. The physical form of the oxidizing agent present in the zone of the first type is variable, but it is preferable that the oxidizing agent be in a substantially particulate form. Particularly preferred is a finely ground powder of oxidizing agent.

The rate of heat produced by the device of the invention under design conditions is tailored by controllably exposing the reactants to each other. This is accomplished by controllably exposing limited amounts of the fuels to the full amount of the oxidizing agent, or by controllably exposing limited amounts of the oxidizing agent to the full amount of the fuels, or by controllably exposing a limited amount of the oxidizing agent to a limited amount of the fuels. In each case, as the reaction proceeds, controlled exposure occurs until the reaction terminates due to lack of one of the reacting components. In preferred embodiments, the dissolvable binding agent dissolves in the solvent and/or the fuels during the exothermic chemical reaction to controllably expose the oxidizing agent to the fuels at a predetermined rate. In a preferred embodiment, an excess of fuel is used. Upon completion of the reaction of the oxidizing agent, there are no soluble toxic or environmentally undesirable residues remaining in the container. Disposal of the container in a landfill is made possible by this feature.

Dispersing the oxidizing agent in a dissolvable binding agent provides an effective means of selectively exposing the oxidizing agent to the fuels. If the reaction takes place in an organic environment with an organic solvent, the binding agent is preferably organic-based. If the reaction takes place in an inorganic environment with a solvent such as water, the binding agent is preferably inorganic-based.

Silicates are suitable inorganic binding agents. In a preferred embodiment, the oxidizing agent is bound within a binding agent comprising aqueous sodium silicate solution ($Na_2SiO_3$), such as that available commercially from J. T. Baker (Stock No. 3877-01) or Aldrich Chemical Co., Inc. (Stock No. 33,844-3).

Uniform distribution of the oxidizing agent throughout the binding agent is preferable in that it provides a consistent, uniform presentation of the oxidizing agent to the fuel through the solubilization of the binding agent. The configuration and geometry of the bound oxidizing agent of the present invention are important factors in providing control over the rate and duration of the reaction. In one preferred configuration, the bound oxidizing agent is in a solid form having a geometry which presents a relatively constant active surface of oxidizing agent to the fuel throughout the desired duration of the reaction and throughout the solubilization of the binding agent, even near oxidizing agent exhaustion. A preferred geometry will also provide necessary fuel around the exposed oxidizing agent at all times during the reaction. Preferably, large fuel migration paths to the oxidizing agent are not required. The binding agent should be diluted to uniformly wet the oxidizing agent crystals. Ratios of binding agent to oxidizing agent of from about 1:1 to about 1:7 can be used in the invention. Preferred ratios are from about 1:1.5 to about 1:5. A ratio of about one gram of binding agent to about three grams of oxidizing agent is used in certain preferred embodiments. This ratio produces a uniform mixture with neither pools of excess binding agent nor oxidizing agent incompletely surrounded by liquid. However, it will be apparent to one skilled in the art that the ratio of binding agent to oxidizing agent may be widely varied.

Techniques for coating the oxidizing agent include spray drying and fluidized bed drying. These techniques are well known to those in the art. Those of skill in the art will be able to determine proper conditions and relevant parameters for producing coated oxidizing agents by these means by routine experimentation. Suitable direction in this field is also given in the '230 patent.

Certain applications of the present invention may require a rapid initial heat-up. This may be accomplished by adding a minor amount of either unbound oxidizing agent crystals or oxidizing agent crystals bound with a dilute binding agent solution to the zone of the first type. The amount is selected to raise a temperature of the contents of the heating system to the desired pre-heat temperature when initially contacted with the fuel. A rapid preheating process is particularly desirable when the present invention is used for food heating devices.

While not wishing to be bound by any particular theory, we believe that upon oxidation of a polyhydroxy fuel by an inorganic oxidizing agent, the pH of the aqueous environment drops to acidic values. We believe that this pH drop triggers the conversion of the preferred inorganic binding agent, sodium silicate, to a gel. This gelation process acts to some degree to moderate the exothermic chemical reactions under intended, or design, conditions.

The fuels are complementary with the oxidizing agent. For most applications, the oxidizing agent and the fuels should conform to applicable governmental standards in case any discharge into the environment occurs, including accidental discharge.

Suitable fuels are soluble solid or liquid organic compounds. Particularly well suited organic compounds are those containing hydroxyl groups. Such groups are easily oxidized to carbonyl-containing compounds by the oxidizing agents described herein. Preferable fuels are sugars or alcohols, and polyhydroxyl-containing compounds which contain at least two hydroxyl groups. Such polyhydroxyl-containing compounds are also readily oxidized to aldehydes, ketones and carboxylic acids. This oxidation of polyhydroxyl-containing compounds and the simultaneous reduction of the oxidizing agent is accompanied by the release of significant amounts of heat energy.

Preferred oxidizable primary fuels in the zone of the second type are liquids. Examples include glycerine, ethylene glycol, propylene glycol, polyethylene glycol, and the like. A preferred primary fuel is glycerine.

According to the processes which moderate the exothermic chemical reactions taking place inside the heat packs of the invention, at least one fuel is required that is present in amounts resulting in at least saturation of the solvent. This fuel may be the only fuel or a secondary fuel. Preferred amounts of this fuel are those creating a reservoir of fuel which is not in solution. This criterion is closely tied to the solubility characteristics of the fuel. Also required is a presence of a vapor space and container surface above the reaction medium upon the walls of which condensation of the solvent can take place. Increases in container temperature that result from a low rate of heat loss vaporize solvent from the reaction medium. The condition of fuel saturation results in fuel being removed from the reaction medium.

The primary fuel can undergo this process in some circumstances. In certain preferred embodiments, however, the primary fuel, glycerine for example, will be highly soluble in the reaction medium over a wide range of concentrations, and will not be removed from the reaction medium. In such cases, evaporation of the solvent does not result in reduction in the amount of primary fuel in the reaction medium. In these embodiments, the saturation condition of a secondary fuel is used to moderate the exothermic reaction.

Secondary fuels which are used in the zone of the first type, are preferably hydroxy-containing fuels. Since this fuel will be in the same zone as the oxidizing agent, it is provided in a form that will not lead to immediate exothermic chemical reaction upon contact with the oxidizing agent. One way to prevent immediate exothermic chemical reaction between the oxidizing agent and the secondary fuels is to provide these fuels as solids. In this way, the initiation of the exothermic chemical reaction is initially dependent upon the creation of a liquid reaction medium, and subsequent solubilization of the secondary fuel.

The secondary exothermic chemical reaction does not occur appreciably until there is temperature rise beyond the anticipated ambient temperature range within the heat pack container. This prevents premature reaction. If the reaction medium is aqueous solvent, the secondary fuels are water soluble. It is desirable that there be multiple hydroxyl groups per fuel molecule, increasing the efficiency of the fuel. The temperature rise from the exothermic reaction of the oxidizing agent with the primary fuel initiates a second stage, or secondary, exothermic chemical reaction.

Polyhydroxyl-containing soluble organic secondary fuels which have been found suitable for use in the zone of the first type are sugars. They are soluble in water and, as described above, are used in amounts preferably exceeding their solubility in the liquid reaction medium. All monosaccharides and many oligosaccharides are generally sugars. The sugars found useful as secondary fuels in the heat packs of the invention are mono- and oligosaccharides sugars, as well as those sugars which are modified and substituted with other groups. Sugars suitable for use as secondary fuels in the zone of the first type in the heat packs of the invention include sucrose, fructose, maltose, lactose, xylose, mannose, glucose, galactose, arabinose, and the like, as well as modified and substituted derivatives of these sugars. A preferable secondary fuel for use in the zone of the first type is sucrose. Sucrose is available from many sources and in many forms including granulated table sugar, powdered confectioner's sugar, brown sugar, and sucrose from sugar cane and sugar beets. Inasmuch as the exothermic chemical reaction does not depend upon the stereochemistry of the fuel for its heat production, any available stereochemistry of fuel molecules is suitable.

The available surface area of the secondary fuels is an important factor in the ready solubility of such fuels in the reaction medium. Surface areas of solids are highly dependent on the physical form of the solid. The physical form of the secondary fuel present in the zone of the first type is variable, but it is preferable that the fuel be in a substantially particulate form. For example, crystals which have a size similar to that found in table sugar are quite suitable. Powdered secondary fuels are also used quite satisfactorily. Persons skilled in the art will understand how, by simple trial and error, to select a particular secondary fuel and particle size to achieve the desired heating characteristic for a particular application.

It is to be understood that although this characterization has been described in terms of reactions between a single oxidizing agent and a number of fuels, the invention is equally effectively put into practice through reactions between a single fuel and a number of oxidizing agents. It is also to be understood that beyond primary and secondary reactions, tertiary, quaternary and further reactions are within the scope of this invention. These reactions would be carried out with tertiary, quaternary and further fuels and/or oxidizing agents. In one of the preferred embodiments of the invention another substance is present within the container of the invention which could act as a tertiary fuel, participating in a third stage reaction, proceeding efficiently only at even higher temperatures.

The heat packs of the invention are provided with a gel present in the zone of the second type which is preformed before compromise of any separator between the zones of different types. The presence of a preformed gel helps moderate the exothermic chemical reactions as soon as the reactions begin. There is no need to await the formation of a gel, through dissolution of gel-producing components, or through the gel-forming reactions of those components. There is also no need to rely on rapidly increasing temperature for the dissolution of gel-producing components or the gel-forming reactions. The amount of gel relative to the amount of secondary fuel is adjusted such that the maximum solubility of the secondary fuel is reached and preferably exceeded. This allows a greater amount of chemical reactants to be loaded into the respective zones of the container, since the exposure of the reactants to each other is limited by the gel. This greater loading capacity permits sustaining peak operating temperatures for longer times. The preformed gel has stiffness which may also moderate the primary exothermic chemical reaction.

The gels useful in the present invention are either organic or inorganic; both types are useful in the present invention. Preferred gels for use in the zone of the second type are organic gels. Useful gels can be formed from organic compounds such as carbohydrates including carbohydrates such as starch; polyacrylamide; polyols such as pentaerythritol; or proteinaceous materials such as gelatin in solvents such as water, acetone, alcohols, dimethoxytetraglycol. Gels can also be formed from inorganic compounds such as metal oxides, metal alkoxides, or alkali metal salts of metal oxides. These include zinc oxide, tin oxide, titanium oxide, zirconium oxide, and silicates and aluminates in solvents such as water and alcohols. Many further examples of organic- and inorganic-based gel systems are known to those skilled in the art. Useful gels increase in stiffness when some of the solvent is removed, i.e., by evaporation.

In one of the preferred embodiments, the gel present in the zone of the second type is an organic-based gel. Especially preferred are aqueous organic-based gels. It has been found that polyhydroxy-containing organic polymer-based gels work well in the heat packs of the invention. A variety of polysaccharides are thus useful in the present invention. Starch gels have been found to be useful in some of the embodiments of the invention. Starch comprises a mixture of linear (amylose) and branched (amylopectin) polymers of α-D-glucopyranosyl units. Amylose is a linear polymer of D-glucopyranosyl units linked to each other by (1→4) α-glucosidic links. Amylopectin is a highly branched polymer of α-D-glucopyranosyl units which are chiefly (1→4) links, but also containing (1→6) α-glucosidic links located at branch points. It is believed that (1→6) α-glucosidic links are more heat resistant than (1→4) α-glucosidic links. Other noncarbohydrate materials isolable from starch include fatty acids, proteins, enzymes, and inorganic materials, which are generally present in small amounts. Starch may be isolated from many sources, including the seeds of corn, waxy corn, wheat, rye, barley, sorghum, or rice, or the roots of such plants as tapioca, potato, or arrowroot, or from the pith of the sago palm tree.

Starches are generally characterized by their gelatinization temperatures, which are the temperatures at which initially thin, opaque starch suspensions become viscous, semiopaque, and finally transparent. Amylose content ranges from almost zero to about 85%, with the majority of the remainder consisting of amylopectin. The thickening of some starch pastes is caused by association of the linear molecules of amylose. Corn starch forms a rigid gel. Potato starch, tapioca, and sago have less tendency to gel. Waxy starches (with unusually low or no amylose) do not gel in dilute dispersions, but at high concentrations (30%) form reversible gels, which redisperse at 50–60° C.

Starches may be modified by crosslinking, to increase shear resistance, heat resistance, and resistance to extremely high or low hydrogen-ion concentrations. Starches may be partially oxidized to yield improved stability. Starches can be derivatized by inorganic esterification with nitrates, sulfates, phosphates or xanthanates, or by organic esterification through treatment with carboxylic acids, acid anhydrides, acid chlorides, or vinyl esters. Starch ethers can also be formed for use in the present invention.

Some organic gels might serve as fuels for the oxidizing agents, due to the presence of oxidizable functional groups such as hydroxyl groups on the gel molecules. If this is the case, a gel is selected which has a reaction rate with the oxidizing agent that is lower than the reaction rate of the oxidizing agents with the primary and secondary fuels chosen for use in embodiments of the invention. Thus, a general requirement for the gelling agents to be used in the heat packs of the invention is that they not be as chemically reactive with the oxidizing agent as are the fuels. It is most desirable that the reaction between the oxidizing agents and the gels do not take place appreciably at temperatures at which the heat packs are designed to operate, or take place slowly over the time scales within which the heat packs are designed to operate. If this requirement is not considered, the gel is likely to be consumed by the exothermic chemical reaction, and the benefits which the gel imparts to the heat packs of the invention would be lost. Starch gels are also susceptible to attack by acids, which tend to hydrolyse the glycosidic linkages and lead to partial or, under more drastic conditions, complete depolymerization of starch. Similarly, high reactivity of the starch to the acidic reaction medium (believed to be found in some of the embodiments of heat packs of the invention) is a consideration in choosing the particular starch.

Detailed information on gelation technology is available, e.g., in scientific publications such as Livage, J. et al., *Prog. Solid St. Chem.*, 18:259 (1988), which is hereby incorporated in its entirety. Starch gelation is described in the Encyclopedia of Polymer Science and Technology, v.12, Interscience; John Wiley & Sons, Inc., New York, 1970, pp. 819–847.

Preferred starches for use in the heat packs of the invention are cold water hydrating starches, which are resistant to acidic conditions and temperatures up to 100° C. Especially preferred are those starches which have viscosities of at least 300 Brabender Units (BU) at 95° C. initially, and at least 400 BU at 95° C. after 15 minutes at that temperature. More preferably, the starches have viscosities of at least 350 BU initially at 95° C., and at least 450 BU after 15 minutes at that temperature. Suitable starches are available as MIRA-THIKO® 468 starch (A. E. Staley Mfg. Co., Decatur, Ill.).

The exothermic reactions taking place in the heat packs of the invention are self-modulating, due to reversible changes in the mechanical properties of the reaction medium, including the preformed gel. These changes take place in response to varying rates of heat loss to the environment or in response to non-optimal ambient temperatures. Removal of solvent from the gel by vaporization and subsequent condensation on condensation surfaces present in the container during operation of the heat pack stiffens the gel. This stiffening reduces the rate of diffusion of the chemical reactants to each other and thereby reduces the rate of exothermic chemical reaction between the oxidizing agent and the fuels. Addition of solvent to the gel reverses this stiffening and increases the rate of diffusion and thereby, the rate of exothermic chemical reaction.

The choice of solvent is based primarily on heat capacity, flash point, vapor pressure and corrosiveness, as the devices can be designed for use at relatively high temperatures. The solvent should not act as a fuel for the oxidizing agents used in the invention. High heat capacities are desirable for efficient operation. High flash points are desirable for safety reasons. Vapor pressures must be sufficient to permit evaporation of solvent upon reaching temperatures which approach the maximum operating temperature ($T_{max}$) of the heat pack. On the other hand, excessively high vapor pressures are undesirable due to safety considerations, since bursting of the container could occur in this case. Low corrosive solvents are desirable so as not to unduly limit the choice of container materials. For many of the preferred embodiments, an appropriate solvent will turn out to be water.

The solvents which are included in the zone of the second type are preferably those which have vapor pressures and boiling points such that evaporation of solvent begins to take place at a temperature range that is intended to be reached upon use of the device. As described below, this property of the solvent is used as a temperature modulation means. For example, the solvent will preferably begin to evaporate as the temperature of the pack begins to climb near to a predetermined maximum operating temperature. This predetermined maximum operating temperature will generally also be a temperature at which the exothermic chemical reaction between the oxidizing agent and the secondary fuel proceeds efficiently. The operating temperature of the heat pack is adjusted to a desired level for an intended heat loss by varying the concentrations of oxidizing agents, fuels and gel. Such adjustment is within the skill in the art. Only routine experimentation is required to select appropriate concentrations for a particular use. Suitable operating temperatures for most applications are within the range of from about 30° C. to about 120° C. Higher and lower operating temperatures may be selected for particular applications. As described more fully below, the evaporation of the solvent acts to reduce the rate of reaction between the oxidizing agent and the fuels. The solvent should not behave as a fuel for the oxidizing agent. A suitable solvent is water.

For the devices of the invention, the solvent is any which can solubilize both the oxidizing agent and the fuels, as well as supporting the preformed and reversibly stiffenable gel. For such inorganic oxidizing agents, for example, alkali metal salts of permanganate, polyhydroxy fuels, and starch-based gels, for example, as described herein, the preferred solvent is water. Water also acts as an excellent heat transfer medium in the present invention. The water used in the present invention can be tap water, although it is preferred to use controlled quality water, such as distilled or deionized water. The most preferred type of water for use in the invention is deionized water.

Concentrations of the reactants are selected to achieve the desired rates of heat generation, peak operating temperatures and $T_{max}$. Persons skilled in the art will know how to vary concentrations until design parameters are achieved. Dilution of the reactants in solvent and lowering their concentrations thereby, limits the contact of the oxidizing agent and the fuel, or fuels. Lowering the concentrations of either the oxidizing agent or the fuels in a solvent will reduce the overall reaction rate, and lower the maximum temperature. Dilution also increases the length of time heat is produced, due to the thermal mass of solvent.

Temperature stabilizing means can be included in the heat pack. Such temperature stabilizing means will permit the heat pack to remain at a given temperature, even if heat transfer is lower than design, or ambient temperature is higher than design. The given temperature which is to be maintained can be the operating temperature, for example.

Suitable temperature stabilizing means include phase change materials. Phase change materials are designed to utilize latent heat absorption associated with a reversible phase change transition, such as a solid-liquid transition. Certain phase change materials also absorb or emit heat upon solid-solid phase transitions. The phase change materials which are preferred for the present invention utilize a reversible solid-liquid transition.

Phase change materials store thermal energy in the form of a physical change of state as the core material melts or freezes or undergoes a solid-solid transition. In order to maintain the ability of the phase change materials to recycle between solid and liquid phases, it is important to prevent dispersal of the phase change materials throughout the solvent (or carrier fluid) when they are in the liquid form. An approach which has found success is encapsulation of the phase change materials within a thin membrane or shell. Such thin membranes or shells should desirably not significantly impede heat transfer into or out of the capsules. The capsules can desirably also be small enough to present a relatively high surface area. This makes rapid heat transfer to and from the carrier fluid possible. Such capsules are known as microcapsules. Microcapsules range in size from about 1.0 to about 1000 microns and are formed according to conventional methods well known to those with skill in the art.

The composition of the phase change material is modified to obtain optimum thermal properties for a given temperature range. For example, the melting point for a series of paraffinic hydrocarbons (normal, straight chain hydrocarbons of formula $C_nH_{2n+2}$) is directly related to the number of carbon atoms as shown in the following table.

TABLE 1

| Compound Name | Carbons | Melting Point (° C.) |
| --- | --- | --- |
| n-tridecane | 13 | −5.5 |
| n-tetradecane | 14 | 5.9 |
| n-pentadecane | 15 | 10.0 |
| n-hexadecane | 16 | 18.2 |
| n-heptadecane | 17 | 22.0 |
| n-octadecane | 18 | 28.2 |
| n-nonadecane | 19 | 32.1 |
| n-eicosane | 20 | 36.8 |
| n-heneicosane | 21 | 40.5 |
| n-docosane | 22 | 44.4 |
| n-tricosane | 23 | 47.6 |
| n-tetracosane | 24 | 50.9 |
| n-pentacosane | 25 | 53.7 |
| n-hexacosane | 26 | 56.4 |
| n-heptacosane | 27 | 59.0 |
| n-octacosane | 28 | 61.4 |
| n-nonacosane | 29 | 63.4 |
| n-triacontane | 30 | 65.4 |
| n-hentriacontane | 31 | 68.0 |
| n-dotriacontane | 32 | 70.0 |
| n-tritriacontane | 33 | 71.0 |
| n-tetratriacontane | 34 | 72.9 |
| n-hexatriacontane | 36 | 76.1 |

In addition to the hydrocarbons listed here, other paraffinic hydrocarbons having a greater (or lesser) number of carbon atoms having a higher (or lower) melting point can also be employed in practicing the invention. Additionally, plastic crystals such as 2,2-dimethyl-1,3-propanediol (DMP) and 2-hydroxymethyl-2-methyl-1,3-propanediol (HMP) and the like are also contemplated for use as the temperature stabilizing means. When plastic crystals absorb thermal energy, the molecular structure is modified without leaving the solid phase. Combinations of any phase change materials can also be utilized.

To allow initiation of the exothermic oxidation reaction, the primary fuel and oxidizing agent must come in contact with each other. This is preferably accomplished in the present invention by opening, selectively perforating, rupturing or otherwise compromising the separator between the zones containing the oxidizing agent and the primary fuel/gel mixture, so that the oxidation reaction partners are able to contact each other. In a preferred embodiment, the primary fuel/gel mixture is transferred into the zone containing the oxidizing agent and the secondary fuel after compromise of the separator. However, it is also contemplated that the oxidizing agent and secondary fuel can be transferred into the zone containing the primary fuel/gel mixture after compromise of the separator. Either zone may contain phase change material.

It is preferred that the separator comprises a material that allows its rupture, perforation, or compromise when the container is manually deformed. In embodiments which comprise more than a single pair of container zones, it is contemplated that the heat pack of the invention comprise an appropriately increased number of separators, so that communication may be established between zones of each type, sufficient to provide the heat desired. A plurality of separators are also possible in embodiments utilizing only a single pair of zones. The invention is not limited by the juxtaposition or configuration of the zones in the heat pack.

Pressure against or along the separator selectively ruptures, perforates, or otherwise compromises the separator, while leaving the outer surfaces of the container, and the surfaces surrounding the container and zones of the first and second types intact. The separator might be comprised of any of a number of functional configurations. In a preferred embodiment, the separator comprises a brittle or weakened wall extending between zones of the first type and zones of the second type, which is manually separable, thereby compromising the separator. In another preferred embodiment, the separator is a brittle or weakened wall of a container comprising a zone of the first type which is adapted to be contained within a zone of the second type.

In another preferred embodiment, the separator is compromised by the use of pull tabs. When pulled, the pull tabs compromise the separator and communication is provided between the oxidizing agent zone and the primary fuel/gel zone. In a less preferred embodiment, the separator comprises a hole with a stopper, which is removable when pressure is applied to it. Communication is again provided through the separator. We most prefer that the separator comprises a wall having weakened or thin areas which rupture when pressure is applied against it. In another embodiment, the separator comprises a wall having a plurality of perforations which rupture under applied pressure and expose the contents of the zones to each other. The separator can likewise consist of a movable disk or cap, pierced or otherwise, or a valve, such as a frangible valve.

Alternatively, the separator is configured to form one or preferably a plurality of fissures or slits when the separator is subjected to external pressure. The fissures can extend inwardly from the edges or perimeter of the separator, or they can be located intermediate the edges or perimeter of the separator. However, any adequate means for compromising the separator is anticipated for use in the present invention. Persons skilled in the art will recognize other possible variants.

The container preferably comprises a flexible material which is not deleteriously affected by any of the contents of the individual zones, and which is resistant to the temperature to be achieved. Such materials can be polymeric, and include polyethylene, polypropylene, polyester (such as MYLAR®, film obtainable from DuPont) aluminum, aluminized polymer film, and other conventional plastic or other packaging materials suitable for containing heated liquids such as rubber, vinyl, vinyl-coated fabric and polyethylene. A thickness of about 0.02 mm to about 0.1 mm has been found to be satisfactory using clear vinyl. This permits the container to act as a thin-walled envelope that conforms to the shape of its surroundings.

The container is preferably constructed of thin, flexible, thermally conductive material comprising an upper layer and a lower layer which are bonded together at the edges to form an hermetically sealed, substantially planar envelope.

Most preferably, the container is vacuum sealed, with the upper and lower layers drawn together. This is especially desirable for the zone of the first type, which contains the bound oxidizing agent, and in certain preferred embodiments, the solid secondary fuel. These dry components are, in certain embodiments, distributed evenly throughout the zone as the zone is vacuum packed. In other embodiments, these components are grouped together in a number of smaller piles of the total amount of bound oxidizing agent and, optionally, the secondary fuel. These piles are themselves distributed evenly throughout the zone as the zone is vacuum packed. These even distributions of the components or piles of components within this zone lead to even heat generation during operation of the device. In preferred embodiments, vacuum packing also allows slight expansion of the zones as the contents of the heat pack react with each other and slight positive gas pressure develops.

This expansion creates the vapor space and surface of the container above the reaction medium which is required for the present invention. This space can be created or made creatable upon operation of the device by a number of other alternative package constructions. Such alternate package construction is within the skill of the art.

In a preferred embodiment, the thermally conductive material is a metal foil, such as one composed substantially of aluminum or copper, or a metallized plastic film such as aluminized polyester, for example MYLAR®. The edges of the material are bonded together by any suitable means, for example, soldering, heat sealing, ultrasonic welding, solvent welding, fold sealing, or the use of adhesives.

During fabrication of the heat pack, the container preferably comprises an open end or side at each of the zones for the introduction of the primary fuel/gel mixture and oxidizing agent/secondary fuel, respectively. The other sides or edges are sealed before this introduction. After addition of the primary fuel/gel and oxidizing agent to the different zones of the container, the open sides are sealed to make the container fluid- and air-tight. The size and shape of the container, as well as the juxtaposition and configuration of zones within the container, will vary according to the application for which it is used. Therefore, alternative assembly procedures are available to properly assemble the heat pack. For example, in certain preferred embodiments, one type zone might be vacuum sealed before the loading of the other type of zone, in e.g., an annular arrangement of zones, or the bag-in-a-bag arrangement. A particular embodiment employs a stacked arrangement of zones. The invention is not limited by the arrangement of zones within the container.

After assembly and prior to its use, the heat pack is in a static condition, with the heat pack preferably disposable after a single use. In an alternative embodiment of the present invention, a plurality of zones of the first and/or second types are contemplated for use in the heat pack of the present invention. As previously mentioned, more than one separator could be used in these embodiments, as well as embodiments having only a single pair of zones.

To use the invention, the user compromises or otherwise opens the separator. The user then manually or otherwise distributes the contents of one zone into the other zone, or vice versa. In preferred embodiments, the contents of the primary fuel/preformed gel/solvent-containing zone are distributed into the bound oxidizing agent/optional secondary fuel-containing zone.

There are a number of applications for which the heat packs of the present invention are useful. Heat is transmitted by convection through the liquid medium in the heat pack to the exterior surfaces of the device, where it is further transmitted to other bodies, according to the specific application for which the heat pack is employed. In such applications, the heat pack is designed to assume the appropriate shapes for these uses. The heat pack is designed to heat food or drink in certain embodiments, for example. The heat pack used to heat food or drink can be designed to meet certain performance criteria such as the attainment of a certain operating temperature within a certain time. For example, the heat pack can be designed to reach 60° C. within twelve minutes. For certain military applications, this performance criterion is critical.

The heat pack of the present invention also finds use in remote wilderness areas for recreational purposes, or in rescue operations in any area, where compact, self-heating devices are desired. The heat pack is readily used to warm shock victims, or to treat or prevent frostbite. Other uses such as the warming of articles of clothing, including gloves, boots and other footwear, are envisioned.

The heat packs of the present invention are easily adapted to be used in surgical or other medical applications, such as in human or veterinary surgery. During surgery, core body temperatures often drop to undesirable levels. The heat pack of the present invention can easily be used to warm patients. Because the present heat packs have excellent temperature stability characteristics, patient discomfort and eventual tissue distress due to overheating are significantly minimized.

For these and other applications, the heat pack preferably includes a fastening means which allows the initial positioning of the heat pack, e.g., onto a limb. Subsequent activation of the device then takes place without further positional adjustment. Suitable fastening means include straps, adhesive tape, or reusable strips such as VELCRO® strips. Such surgical applications are readily be fulfilled if the heat pack is designed as a sleeve which is dimensioned to be placed around a limb, such as the leg of a human, horse, dog, or any other animal for which veterinary surgery is carried out. Or flat heat packs can be inserted into a fabric sleeve or wrap. Desirably, the sleeve diameter is adjustable, permitting the use of the same sleeve on a variety of patients. Alternately, the heat pack is designed as a pad, allowing extensive bodily surfaces such as the back or chest of a human or animal to be heated. The heat pack may be activated either before or after contact with the object to be heated in any of the applications for which the heat pack can be used, according to convenience to the user. The term "activation" as used herein refers to compromise or other operation of the separator, mixing the contents of the zones of the disposable container, and thereby initiating exothermic chemical reaction, as well as manual or other mixing of the contents of the heat pack together to ensure even distribution of the contents and therefore, even heating.

The heat pack of the present invention is easily adapted to be used in therapeutic applications. Many types of injury are most desirably treated through the application of heat. These include muscle and ligament strains and sprains, as well as such afflictions as rheumatism, arthritis, and the like. Such applications of the heat pack would also require the heat pack to be fashioned as a sleeve or a pad, and include fastening means, such as those described above.

The invention also features a method of heating an object with a self-heating, disposable liquid heat pack. The method consists of providing a heat pack such as described above, activating the heat pack by compromising the separator, manually or otherwise mixing the contents of zones of the first and second types together to insure contact of their contents, and subsequently putting the exothermic reaction thereby initiated to practical use in heating an object. This is most effectively accomplished by establishing and maintaining thermal contact between the object and the heat pack. In some embodiments, the heat pack is integral with a container for a substance to be heated, such as a container for food or drink. In other embodiments, the heat pack is simply added on to the object to be heated, or adapted to be fit to the object to be heated.

The invention will be further described in the following examples, which do not limit the scope of the invention described in the claims.

EXAMPLES

The following examples are illustrative of some specific embodiments of the invention, and performance characteristics of the invention.

Example

Heat Pack for Use with a Ready-to-Eat Meal

A heat pack for use with a portable meal was prepared as follows. A vinyl container measuring about 8×10 inches was prepared, and when filled and sealed, the container's thickness was substantially thinner than either of its other dimensions. The container had a zone of the first type for the bound oxidizing agent and secondary fuel, a zone of the second type for the primary fuel and starch gel solution, and a frangible seal between the oxidizing agent zone and the fuel zone. The zones contained the following ingredients: the zone of the first type contained 20 grams of powdered sugar and 27 grams of 100 mesh particles of bound oxidizing agent, prepared as follows.

The oxidizer (23.7 g potassium permanganate powder) was mixed with 13 mL of 25% by weight sodium silicate solution made up by diluting 42 Baume sodium silicate solution with water to dissolve precipitated solids. The mixture was spread onto a flat surface and dried into a sheet, which was subsequently reground into 100 mesh particles for use in the invention.

The dry, bound oxidizer (potassium permanganate/sodium silicate) and powdered sugar were intimately mixed and spread evenly over the inner surface of one face of the pouch. In alternate embodiments, these dry ingredients were divided into several porous, easily wetted inner bags, rather than being spread over a horizontal surface. These bags were able to fluidly communicate with each other via thin absorbent material which was able to transmit the fluid ingredients to each inner bag. The fluid were able to wick through the absorbent material and wet the contents of each inner bag. The inner bags comprised the zone of the first type.

16.7% by volume glycerine and 1.5 grams Mira-Thik® 468 starch were solubilized in 68 ml deionized water for the zone of the second type. This zone was sealed and placed along one end of the pouch. The entire outer bag was then evacuated in order to keep the dry ingredients in place, as well as to aid in the distribution of the liquid components upon breach of the seal between the zones. The container was sealed and was thereafter ready for use.

Upon activation of the heat pack by compromising the frangible seal, the heat pack reached an operating temperature of approximately 95° C. within two minutes. This operating temperature was maintained for approximately 90 minutes, after which the device cooled back to ambient temperature over the course of 180 minutes.

We have successfully tested other embodiments of the heat pack of the invention for other applications. For human therapy, a heat pack of the same size was designed and produced. For this heat pack, the ingredients and method of preparation were the same, except that 3 grams of starch were used. Upon operation, this heat pack exhibited an operating temperature of 40° C. within two minutes. This operating temperature was maintained for approximately 200 minutes. Of course, other sealing materials and arrangements are possible.

Another embodiment of the invention utilized 27 grams of coated oxidizer powder, and 20 grams of powdered sugar in the first zone, and 68 mL of 33% by volume glycerine solution, and 1.5 grams of starch in the second zone. This pack reached approximately 105° C. within 5 minutes and remained stable at that temperature for over an hour.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A disposable heating device comprising:
   a disposable container having at least one liquid-impermeable first zone and at least one liquid-impermeable second zone;
   a separator disposed between the at least one first zone and the at least one second zone, the separator being operable to provide communication between said zones;
   a mixture comprising a primary fuel, a preformed stiff-enable gel, and a vaporizable solvent in the at least one second zone; and
   a substantially solid and particulate oxidizing agent in the at least one first zone, said oxidizing agent being embedded and dispersed throughout solid pieces of a binding agent dissolvable in at least one of said solvent and said primary fuel,
   wherein communication between the first and second zones allows mixing of the contents therein and at ambient temperature initiates a primary exothermic chemical reaction producing heat in said container,
   wherein the dissolvable binding agent dissolves during said exothermic chemical reaction to controllably expose said particulate oxidizing agent at a predetermined rate,
   wherein the container includes a vapor space and a condensation surface above the contents of the zones after communication between the zones is provided,
   wherein the vaporizable solvent vaporizes into the vapor space and condenses on the condensation surface when the temperature of the device approaches a predetermined maximum temperature during operation of the device, causing stiffening of the gel, and
   wherein the amount of said preformed stiffenable gel is sufficient to prevent said exothermic chemical reaction from causing the temperature of the container to overshoot the predetermined maximum temperature during operation of the device.

2. The heating device of claim 1, wherein the container comprises a thin-walled envelope that conforms to the shape of its surroundings.

3. The heating device of claim 2, wherein the container comprises a polymeric material.

4. The heating device of claim 1, wherein the oxidizing agent comprises an alkali metal salt of permanganate.

5. The heating device of claim 1, wherein the vaporizable solvent is water and said primary exothermic chemical reaction occurs in an aqueous environment.

6. The heating device of claim 1, further comprising a temperature stabilizing means in at least one of the zones.

7. The heating device of claim 6, wherein the temperature stabilizing means comprises a phase change material.

8. The heating device of claim 1, wherein the preformed stiffenable gel comprises an organic material.

9. The heating device of claim 8, wherein the organic material is starch.

10. The heating device of claim 1, wherein the primary fuel comprises glycerin.

11. The heating device of claim 1, further comprising a plurality of zones of the first type and a plurality of zones of the second type.

12. The heating device of claim 1, wherein the separator is a single-use, frangible membrane.

13. The heating device of claim 1, wherein the exothermic chemical reaction is a reduction-oxidation reaction.

14. The heating device of claim 1, further comprising a secondary fuel in the at least one first zone, wherein the secondary fuel is soluble in the solvent, and wherein the primary exothermic chemical reaction heats the device to a temperature which initiates a secondary exothermic chemical reaction.

15. The heating device of claim 14, wherein the secondary fuel is substantially solid and particulate.

16. The heating device of claim 14, wherein the container comprises a thin-walled envelope that conforms to the shape of its surroundings.

17. The heating device of claim 16, wherein the container comprises a polymeric material.

18. The heating device of claim 14, wherein the oxidizing agent comprises an alkali metal salt of permanganate.

19. The heating device of claim 14, wherein the binding agent is sodium silicate.

20. The heating device of claim 14, wherein the vaporizable solvent is water and said primary and secondary exothermic chemical reactions occur in water.

21. The heating device of claim 14, further comprising a temperature stabilizing means in at least one of the zones.

22. The heating device of claim 21, wherein the temperature stabilizing means comprises a phase change material.

23. The heating device of claim 14, wherein the preformed stiffenable gel comprises an organic material.

24. The heating device of claim 23, wherein the organic material is starch.

25. The heating device of claim 14, wherein the primary fuel comprises a polyhydroxy compound and the secondary fuel comprises a polyhydroxy compound.

26. The heating device of claim 25, wherein the primary fuel comprises glycerine.

27. The heating device of claim 25, wherein the secondary fuel comprises a sugar.

28. A method of heating objects, comprising the steps of:
   a) providing the disposable heating device of claim 1;
   b) contacting said device with an object to be heated;
   c) compromising the separator to permit contact between the zones; and
   d) mixing the contents of the first and second zones together to insure contact of their contents thereby initiating an exothermic chemical reaction.

29. The method of claim 28, wherein steps c) and d) are performed before performance of step b).

30. The method of claim 28, wherein the object to be heated is a container containing food or drink.

31. The method of claim 28, wherein the object to be heated is a part of the body of a human or animal.

32. The method of claim 31, wherein the human or animal is a medical patient.

33. The method of claim 28, wherein the object to be heated is an article of clothing or footwear.

34. A disposable heating device comprising:
   a disposable container having at least one liquid-impermeable first zone and at least one liquid-impermeable second zone;
   a separator disposed between the at least one first zone and the at least one second zone, the separator being operable to provide communication between the zones,
   a mixture comprising glycerine, a preformed stiffenable starch gel and water in the at least one second zone; and particles of potassium permanganate and sugar in the at least one first zone, said particles of potassium permanganate being embedded in and dispersed throughout solid pieces of sodium silicate, wherein communication between the first and second zones allows mixing of the contents therein and initiates an exothermic reduction/oxidation reaction, producing heat in said container, wherein the solid pieces of sodium silicate dissolves during said exothermic reaction to controllably expose said particles of potassium permanganate at a predetermined rate, wherein the container includes a vapor space and a condensation surface above the contents of the zones after communication between the zones is provided, wherein the water vaporizes into the vapor space and condenses on the condensation surface when the temperature of the device approaches a predetermined maximum temperature during operation of the device, causing stiffening of the starch gel, and and wherein the amount of said preformed stiffenable starch gel is sufficient to prevent said exothermic chemical reaction from causing the temperature of the container to overshoot the predetermined maximum temperature during operation of the device.

35. The heating device of claim 34, wherein the separator comprises a single-use frangible membrane.

* * * * *